United States Patent [19]

Schriewer et al.

[11] Patent Number: 4,977,263

[45] Date of Patent: Dec. 11, 1990

[54] PROCESS FOR PREPARING 1,8-BRIDGED 4-QUINOLONE-3-CARBOXYLIC ACID ANTIBACTERIALS

[75] Inventors: Michael Schriewer, Odenthal; Klaus Croche, Glanthal; Hans-Jonchim Zeiler, Valbert; Karl G. Hetzner, Wuppertal, all of Fed. Rep. of Germany

[73] Assignee: Bayer Aktiengesellschaft, Leverkusen, Fed. Rep. of Germany

[21] Appl. No.: 412,975

[22] Filed: Sep. 25, 1989

Related U.S. Application Data

[62] Division of Ser. No. 272,619, Nov. 17, 1988, Pat. No. 4,902,795, which is a division of Ser. No. 108,839, Oct. 15, 1987, Pat. No. 4,841,059.

[30] Foreign Application Priority Data

Jan. 15, 1986 [DE] Fed. Rep. of Germany ....... 3600891

[51] Int. Cl.$^5$ ................. C07D 237/00; C07D 239/02; C07D 241/00; C07D 241/02
[52] U.S. Cl. ................................. 544/329; 544/224; 544/316; 544/317; 544/319; 544/327; 544/239; 544/335; 544/336; 544/408
[58] Field of Search ............... 544/326, 335, 239, 224, 544/316, 317, 319, 327, 329, 336, 408

[56] References Cited

U.S. PATENT DOCUMENTS

| | | | |
|---|---|---|---|
| 4,499,270 | 2/1985 | Gerster | 544/344 |
| 4,540,694 | 9/1985 | Chu | 544/99 |
| 4,542,133 | 9/1985 | Chu | 544/99 |
| 4,602,017 | 7/1986 | Sawyer et al. | 544/182 |
| 4,607,232 | 8/1986 | Chu | 544/58.6 |
| 4,659,734 | 4/1987 | Enomoto et al. | 544/54 |
| 4,708,732 | 11/1987 | Carter | 544/326 |

*Primary Examiner*—John M. Ford
*Assistant Examiner*—Robert C. Whittenbaugh
*Attorney, Agent, or Firm*—Sprung Horn Kramer & Woods

[57] ABSTRACT

Antibacterially active new 1,8-bridged 4-quinolone-3-carboxylic acid derivatives of the formula

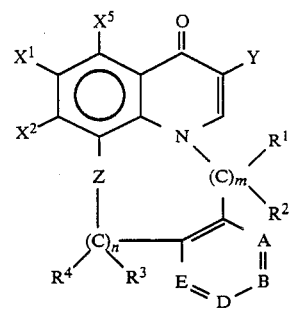

in which
Y is carboxyl or a derivative thereof
$R^1$, $R^2$, $R^3$, $X^1$, $X^2$ and $X^5$ are H or various radicals,
Z is Om NH, substituted NH,

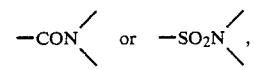

m and n are 0 or 1, and
A, B, D and E are CH or substituted C or up to three of them are N, and physiologically acceptable salts thereof. Novel intermediates are described as well as processes for making the intermediates and end products.

1 Claim, No Drawings

PROCESS FOR PREPARING 1,8-BRIDGED 4-QUINOLONE-3-CARBOXYLIC ACID ANTIBACTERIALS

This is a division of application Ser. No. 272,619, filed Nov. 17, 1988, now U.S. Pat. No. 4,902,795, which is a division of Ser. No. 108,839, filed Oct. 15, 1987, now U.S. Pat. No. 4,841,059.

The invention relates to a new process for the preparation of new 1,8-bridged 4-quinolone-3-carboxylic acids, and to their use as medicaments, in particular as antibacterial agents in human and veterinary medicine, and as an intermediate product for antibacterial agents.

European Patent Application No. 0,004,279 describes the preparation of 4-pyridone-3-carboxylic acids by reaction of enamines, which are capable of tautomerism, with o-halogeno-aryl-carboxylic acid halides and subsequent cyclization in the presence of a base.

New 1,8-bridged 4-quinolone-3-carboxylic acids and derivatives of the formula I

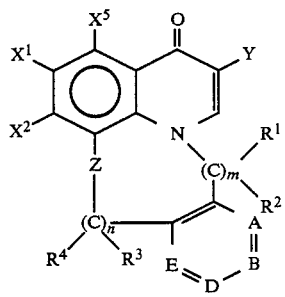

in which
Y represents a carboxyl group, a nitrile group, an ester group —COOR$^5$ or an acid amide group —CONR$^6$R$^7$,
wherein
R$^5$ represents $C_1$–$C_4$-alkyl and
R$^6$ and R$^7$ represent hydrogen or $C_1$–$C_4$-alkyl, and
R$^6$ can also optionally be phenyl,
X$^1$ represents hydrogen, nitro, alkyl with 1–3 carbon atoms or halogen, preferably fluorine,
X$^2$ denotes halogen, preferably fluorine or chlorine, alkyl with 1–3 carbon atoms, an alkylsulphonyl group with up to 3 Carbon atoms in the alkyl radical or a phenylsulphonyl group which is optionally substituted in the aryl radical,
X$^5$ can be hydrogen, halogen or methyl,
Z represents oxygen or an amine radical NR$^8$,
wherein
R$^8$ denotes hydrogen, or an alkyl radical which has 1–6 carbon atoms and is optionally substituted by halogen, trifluoromethyl, cyano, hydroxyl, alkoxy or alkylmercapto with 1–3 carbon atoms, aryloxy, arylthio or an ester radical with 1–3 radical which is optionally substituted by halogen, nitro group or an alkyl group with 1–3 carbon atoms, or furthermore represents an acyl radical R$^9$CO— or R$^{10}$SO$_2$—,
wherein
R$^9$ and R$^{10}$ represent alkyl radicals with 1–6 carbon atoms or optionally substituted phenyl radicals, or Z can be a

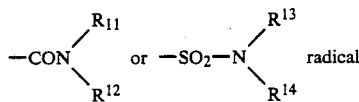

wherein
the radicals R$^{11}$ to R$^{14}$ represent hydrogen, alkyl with 1–6 carbon atoms or an optionally substituted phenyl radical,
R$^1$, R$^2$, R$^3$ and R$^4$ represent hydrogen or alkyl groups with 1–3 carbon atoms, or represent phenyl radicals which are optionally substituted by halogen, nitro or alkyl with up to 3 carbon atoms, and
n and m each denote 0 or 1 and
the symbols A, B, D and E represent C-R$^{15}$ or up to three of these symbols represent nitrogen,
wherein
R$^{15}$ represents hydrogen, alkyl-, alkoxy-, alkylmercapto with in each case 1–3 carbon atoms, halogen, nitro, trifluoromethyl, cyano, carboxyl which is esterified by $C_1$–$C_4$-alkyl, or benzyl or phenyl, each of which can be substituted by $C_1$–$C_3$-alkyl, nitro or halogen,
with useful pharmaceutical properties have now been found.

The invention also relates to physiologically acceptable salts or prodrug forms.

The compounds according to the invention are obtained by a process in which the enamines of the formula II

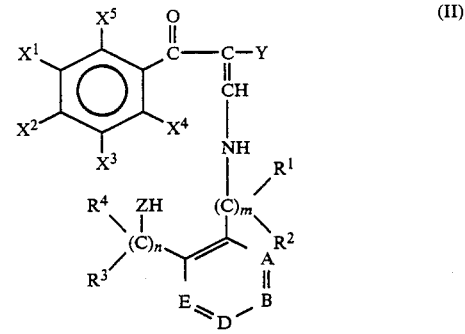

in which
X$^1$, X$^2$, X$^5$, R$^1$–R$^4$, A, B, D, E, Y, Z, m and n have the abovementioned meaning,
X$^3$ represents halogen, preferably fluorine or chlorine, or the nitro group and
X$^4$ denotes halogen, preferably fluorine or chlorine, a nitro group, an alkoxy, alkylmercapto or alkylsulphonyl group with in each case 1–3 carbon atoms or an arylsuphonyl group
are reacted in a first reaction stage in an anhydrous aprotic solvent in the presence of one equivalent of a base to give the 4-quinolone-3-carboxylic acid derivatives of the formula III

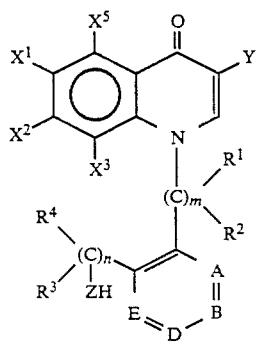

(III)

and the second cyclization is carried out in a second reaction stage in the presence of a further equivalent of a base to give the 1,8-bridged 4-quinolone-3-carboxylic acid derivatives of the formula I, and, if appropriate, the group Y is converted into the carboxyl group in a manner which is known per se, and, if appropriate, this is converted into its alkali metal, alkaline earth metal or silver salts.

The reaction of the enamines II with 2 equivalents of a base without intermediate isolation of III in a so-called one-pot reaction to give the 1,8-bridged 4-quinolone-3-carboxylic acid derivatives I is particularly advantageous.

It is to be described as decidedly surprising that the 1,8-bridging in the second reaction stage of the process according to the invention takes place with participation of a leaving group $X^3$ which is not activated by a carboxyl group in the meta-position.

If the enamino ester 1 is used as the starting substance, the course of the reaction can be represented by the following equation (1→1 '→1 ''→1 '''):

Z, A, B, D, E, n and m having the abovementioned meaning.

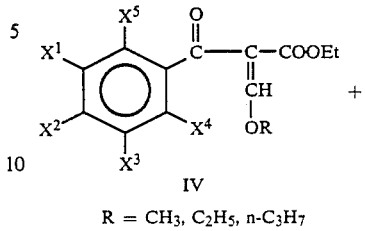

$R = CH_3, C_2H_5, n\text{-}C_3H_7$

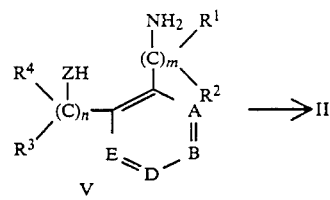

The enol ethers IV are known or can be prepared in accordance with the following general equation:

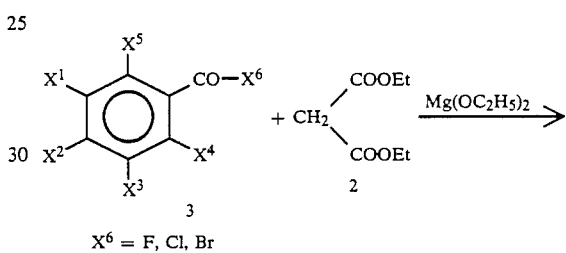

$X^6 = F, Cl, Br$

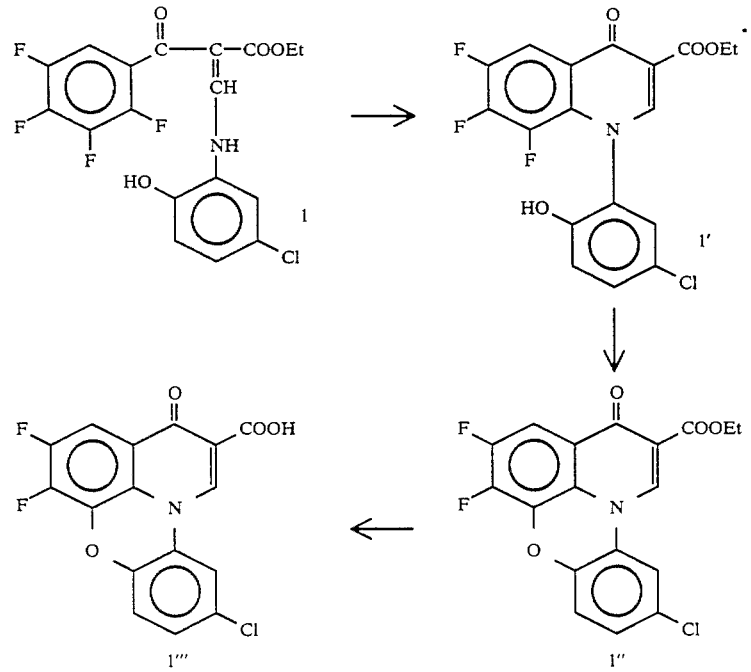

The enamines II used as starting substances are new and can be prepared by reacting the corresponding enol ethers IV with the primary amines V, $X^1$-$X^5$, $R^1$-$R^4$, Y,

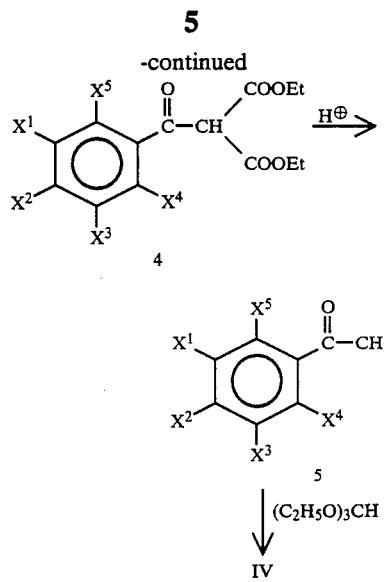

According to this equation, diethyl malonate 2 is acylated with the corresponding benzoyl halide 3 in the presence of magnesium ethylate to give the acylmalonic acid ester 4 (Organicum, 3rd edition 1964, page 438).

Partial hydrolysis and decarboxylation of 4 in an aqueous medium with catalytic amounts of sulphuric acid or 4-toluenesulphonic acid gives a good yield of the acylacetic acid ethyl ester 5, which is converted into the 2-benzoyl-3-ethoxyacrylic acid ethyl ester (IV, R=C₂H₅) with triethyl orthoformate/acetic anhydride. The reaction of (IV) with the amines (V) in a solvent, such as, for example, methylene chloride, an alcohol, chloroform, cyclohexane or toluene, leads to the desired intermediate products (II) in a slightly exothermic reaction. The cyclization reactions (II)→(III), (III)→(I) and (II)→(I) are carried out in a temperature range of about 60°–300° C., preferably 80°–180° C.

Dioxane, dimethylsulphoxide, N-methylpyrrolidone, sulpholane, hexamethylphosphoric acid triamide and, preferably, N,N-dimethylformamide can be used as diluents.

The cyclocondensations can be carried out under normal pressure, but also under increased pressure. The reaction is in general carried out under pressures between about 1 and about 100 bar, preferably 1 and 10 bar.

Possible acid-binding agents for the cyclization reactions (II)→(III), (III)→(I) and (II)→(I) are potassium tert.-butanolate, 1,4-diaza-bicyclo[2,2,2]octane (DABCO), 1,8-diaza-bicyclo[5,4,0]-undec-7-ene (DBU), butyl-lithium, lithium-phenyl phenyl-magnesium bromide, sodium methylate, sodium hydride and sodium carbonate or potassium carbonate. Potassium fluoride or sodium fluoride are particularly preferred if hydrogen fluoride has to be split off.

In each case 1 equivalent of base is in general used for the primary cyclization (II)→(III) and the second cyclization (III)→(I). If both cyclization reactions are combined in a "one-pot reaction" (II)→(I), 2 equivalents of the abovementioned bases must be employed. It may be advantageous to use an excess of 10 mol % of base in the cyclocondensations (III)→(I) and (II)→(I).

The hydrolysis of the esters, nitriles and amides (I) to the corresponding carboxylic acids which takes place in the last step can be carried out under the customary known acid or basic conditions.

The 2,3,4,5-tetrafluorobenzoyl chloride and pentafluorobenzoyl chloride used as starting substances for this synthesis route are known.

3,5-Dichloro-2,4-difluoro-benzoyl fluoride (boiling point 97°/20 mbar; $n_D^{20} = 1.5148$) and 5-chloro-2,3,4-trifluorobenzoyl fluoride (boiling point 66°–70°/20 mbar; $n_D^{20} = 1.4764$) are obtained side by side by heating tetrachlorobenzoyl chloride to elevated temperatures with potassium fluoride in sulpholane:

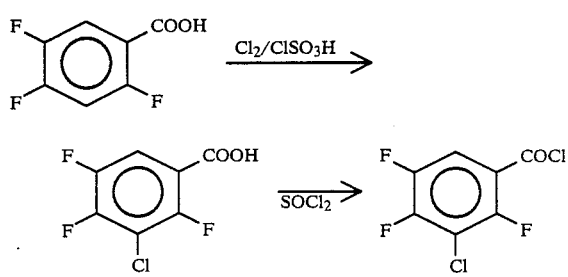

Chlorination of 2,4,5-trifluorobenzoic acid in chlorosulphonic acid leads to 3-chloro-2,4,5-trifluorobenzoic acid, which is reacted as a crude product with thionyl chloride to give 3-chloro-2,4,5-trifluorobenzoyl chloride (boiling point 94°/18 mbar; $n_D^{20} = 1.5164$):

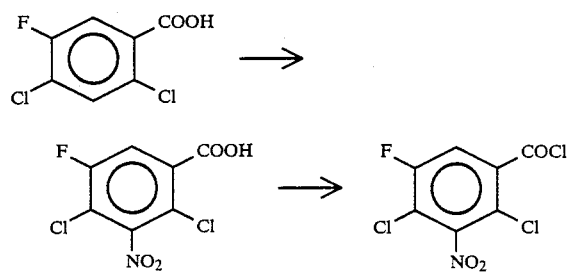

2,4-Dichloro-5-fluoro-3-nitro-benzoyl chloride is obtained by nitration of 2,4-dichloro-5-fluoro-benzoic acid, which is known, to 2,4-dichloro-5-fluoro-3-nitrobenzoic acid and reaction thereof with thionyl chloride.

The amines of the formula V used as starting substances are known. Examples which may be mentioned are: 2-aminophenol, 2-amino-4-chloro-phenol, 2-amino-4-fluorophenol, 2-amino-5-fluoro-phenol, 2-amino-4-trifluoromethyl-phenol, 2-amino-4-nitro-phenol, 2-amino-3-hydroxypyridine, N-acetyl-phenylene-diamine, 2-hydroxy-benzylamine, 2-amino-benzyl alcohol and 2-hydroxymethyl-benzylamine.

The new active compounds have bactericidal properties and can also be used as intermediate products for highly active antibacterial agents.

| Example of a tablet according to the invention | |
|---|---|
| Each tablet contains: | |
| Compound of Example 28 | 583.0 mg |
| Microcrystalline cellulose | 55.0 mg |
| starch | 72.0 mg |
| Insoluble poly-(1-vinyl-2-pyrrolidone) | 30.0 mg |
| Highly disperse silicon dioxide | 5.0 mg |
| Magnesium stearate | 5.0 mg |
|  | 750.0 mg |
| The lacquer shell containes: | |
| Poly-(O-hydroxypropyl-O-methyl)-cellulose 15 cp | 6.0 mg |
| Macrogol 4000 recommended INN polyethylene glycols (DAB) | 2.0 mg |
| Titanium (IV) oxide | 2.0 mg |
|  | 10.0 mg |

The compounds according to the invention exhibit a broad antibacterial spectrum against Gram-positive and Gram-negative germs, in particular against Enterobacteriaceae; above all also against those which are resistant towards various antibiotics, such as, for example, penicillins, cephalosporins, aminoglycosides, sulphonamides and tetracyclines, coupled with a low toxicity.

These useful properties enable them to be used as chemotherapeutic active compounds in medicine and as substances for preserving inorganic and organic materials, in particular all kinds of organic materials, for example polymers, lubricants, paints, fibers, leather, paper and wood, and foodstuffs and water.

The compounds according to the invention are active against a very broad spectrum of micro-organisms. With the aid of these compounds, Gram-negative and Gram-positive bacteria and bacteria-like micro-organisms can be combated and the diseases caused by these pathogens can be prevented, alleviated and/or cured.

The compounds according to the invention are particularly active against bacteria and bacteria-like microorganisms. They are therefore particularly suitable in human and veterinary medicine for the prophylaxis and chemotherapy of local and systemic infections caused by these pathogens.

For example, local and/or systemic diseases which are caused by the following pathogens or by mixtures of the following pathogens can be treated and/or prevented: Gram-positive cocci, for example Staphylococci (*Staph. aureus* and *Staph. epidermidis*) and Streptococci (*Strept. agalactiae, Strept. faecalis, Strept. pneumoniae* and *Strept. pyogenes*); Gram-negative cocci *(Neisseria gonorrhoeae)* and Gram-negative rod-shaped bacilli, such as Enterobacteriaceae, for example *Escherichia coli, Haemophilus influenzae,* Citrobacter (*Citrob. freundii* and *Citrob. divernis*), Salmonella and Shigella; and furthermore Klebsiellae (*Klebs. pneumoniae* and *Klebs. oxytoca*), Enterobacter (*Ent. aerogenes* and *Ent. agglomerans*), Hafnia, Serratia (*Serr. marcescens*), Proteus (*Pr. mirabilis, Pr. rettgeri* and *Pr. vulgaris*), Providencia, Yersinia and the genus Acinetobacter. The antibacterial spectrum also includes the genus Pseudomonas (*Ps. aeruginosa* and *Ps. maltophilia*) as well as strictly anaerobic bacteria, such as, for example, *Bacteroides fragilis,* representatives of the genus Peptococcus, Peptostreptococcus and the genus Clostridium; and furthermore Mycoplasma (*M. pneumoniae, M. hominis* and *M. urealyticum*) and mycobacteria, for example *Mycobacterium tuberculosis*.

The above list of pathogens is merely by way of example and is in no way to be interpreted as limiting. Examples which may be mentioned of diseases which can be caused by the pathogens or mixed infections mentioned and can be prevented, alleviated or cured by the compounds according to the invention are: infectious diseases in humans, such as, for example, otitis, pharyngitis, pneumonia, peritonitis, pyelonephritis, cystitis, endocarditis, systemic infections, bronchitis (acute and chronic), septic infections, diseases of the upper respiratory tract, diffuse panbronchiolitis, pulmonary emphysema, dysentery, enteritis, abscesses of the liver, urethritis, prostatitis, epididymitis, gastrointestinal infections, bone and joint infections, cystic fibrosis, skin infections, postoperative wound infections, abscesses, phlegmons, wound infections, infected burns, burn wounds, infections in the oral region, infections following dental operations, osteomyelitis, septic arthritis, cholecystitis, peritonitis with appendicitis, cholangitis, intraabdominal abscesses, pancreatitis, sinusitis, mastoiditis, mastitis, tonsillitis, typhoid fever, meningitis and infections of the nervous system, salpingitis, endometritis, genital infections, pelveoperitonitis and eye infections.

As well as on humans, bacterial infections can also be treated on other species. Examples which may be mentioned are: pigs: coli-diarrhoea, enterotoxaemia, sepsis, dysentery, salmonellosis, metritis-mastitis-agalactiae syndrome and mastitis; ruminants (cattle, sheep, goats): diarrhoea, sepsis, bronchopneumonia, salmonellosis, pasteurellosis, mycoplasmosis and genital infections; horses: bronchopneumonia, joint ill, puerperal and post-puerperal infections and salmonellosis; dogs and cats: bronchopneumonia, diarrhoea, dermatitis, otitis, urinary tract infections and prostatitis; poultry (chicken, turkeys, quail, pigeons, ornamental birds and others): mycoplasmosis, *E. coli* infections, chronic infections of the respiratory tract, salmonellosis, pasteurellosis and psittacosis.

Bacterial infections in the breeding and rearing of stock and ornamental fish can likewise be treated, the antibacterial spectrum being increased beyond the above-mentioned pathogens to further pathogens, such as, for example, Pasteurella, Brucella, Campylobacter, Listeria, Erysipelothrix, Corynebacteria, Borellia, Treponema, Nocardia, Rickettsia and Yersinia.

The present invention includes pharmaceutical formulations which, in addition to non-toxic, inert pharmaceutically suitable excipients, contain one or more compounds according to the invention or which consist of one or more active compounds according to the invention, and processes for the preparation of these formulations.

The present invention also includes pharmaceutical formulations in dosage units. This means that the formulation is in the form of individual parts, for example tablets, dragees, capsules, pills, suppositories and ampules the active compound content of which correspond to a fraction or a multiple of an individual dose. The dosage units can contain, for example, 1, 2, 3 or 4 individual doses or $\frac{1}{2}$, $\frac{1}{3}$ or $\frac{1}{4}$ of an individual dose. An individual dose preferably contains the amount of active compound which is given in one administration and which usually corresponds to a whole, one half, one third or one quarter of a daily dose.

Non-toxic, inert pharmaceutically suitable excipients are to be understood as meaning solid, semi-solid or liquid diluents, fillers and formulation auxiliaries of all types.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silicic acid, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate, magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only or preferentially in a certain part of the intestinal tract, optionally in a delayed manner, examples of embedding compositions which can be used being polymeric substances and waxes.

The active compound or compounds can also be in micro-encapsulated form, if appropriate with one or more of the abovementioned excipients.

Suppositories can contain, in addition to the active compound or compounds, the customary water-soluble or water-insoluble excipients, for example polyethylene glycols and fats, for example cacao fat and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silicic acid, talc and zinc oxide, or mixtures of these substances.

Powders and sprays can contain, in addition to the active compound or compounds, the customary excipients, for example lactose, talc, silicic ac d, aluminium hydroxide, calcium silicate and polyamide powder, or mixtures of these substances. Sprays car additionally contain the customary propellants, for example chlorofluorohydrocarbons.

Solutions and emulsions can ccntain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, oorn germ oil, olive oil, castor oil and sesame oil, glycerol, glycerolformal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol and propylene glycol, suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain colouring agents, preservatives and additives which improve the smell and taste, for example peppermint oil and eucalyptus oil, and sweeteners, for example saccharin.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also contain other pharmaceutical active compounds in addition to the compounds according to the invention.

The abovementioned pharmaceutical formulations are prepared in the customary manner by known methods, for example by mixing the active compound or compounds with the excipient or excipients.

The formulations mentioned can be used on humans and animals either orally, rectally, parenterally (intravenously, intramuscularly or subcutaneously), intracisternally, intravaginally, intraperitoneally or locally (powders, ointments or drops), and for the therapy of infections in hollow cavities and body cavities. Possible suitable formulations are injection solutions, solutions and suspensions for oral therapy, gels, infusion formulations, emulsions, ointments or drops. Ophthalmological and dermatological formulations, silver salts and other salts, ear drops, eye ointments, powders or solutions can be used for local therapy. In the case of animals, intake can also be via the feed or drinking water in suitable formulations. It is furthermore possible to use gels, powders, dusts, tablets, sustained release tablets, premixes, concentrates, granules, pellets, tablets, boli, capsules, aerosols, sprays and inhalates on humans and animals. The compounds according to the invention can furthermore be incorporated into other carrier materials, such as, for example, plastics (chains of plastic for local therapy), collagen or bone cement.

In general it has proved advantageous both in human and in veterinary medicine to aiminister the active compound or compounds according to the invention in total amounts of about 0.5 to about 500, preferably 5 to 100 mg/kg of body weight every 24 hours, if appropriate in the form of several individual doses, in order to achieve the desired results. An individual dose oreferably contains the active compound or compounds according to the invention in amounts of about 1 to about 80, in particular 3 to 30 mg/kg of body weight. However, it may be necessary to deviate from the dosages mentioned, and in particular to do so as a function of the nature and body weight of the subject to be treated, the nature and severity of the disease, the nature of the formulation and of the administration of the medicament and the period or interval within which administration takes place.

Thus it can in some cases be sufficient to manage with less than the abovementioned amount of active compound, whilst in other cases the abovementioned amount of active compound must be exceeded. The particular optimum dosage required and the mode of administration of the active compounds can easily be determined by anyone skilled in the art on the basis of his expert knowledge.

The new compounds can be administered in the customary concentrations and formulations together with the feed or with feed formulations or with the drinking water. Infection by Gram-negative or Gram-positive bacteria can thereby be prevented, alleviated and/or In general it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual doses, in order to achieve the desired results. An individual dose preferably contains the active compound or compounds according to the invention in amounts of about 1 to about 80, in particular 3 to 30 mg/kg of body weight. However, it may be necessary to deviate from the dosages mentioned, ard in particular to do so as a function of the nature and body weight of the subject to be treated, the nature and severity of the disease, the nature of the formulatior and of the administration of the medicament and the period or interval within which administration takes place.

Thus it can in some cases be sufficient to manage with less than the abovementioned amouht of active compound, while in other cases the abovementioned amount of active compound must be exceeded. The particular optimum dosage required and the mode of administration of the active compounds can easily be determined by anyone skilled in the art on the basis of his expert knowledge.

The new compounds can be administered in the customary concentrations and formulations together with the feed or with feed formulations or with the drinking water. Infection by Gram-negative or Gram-positive bacteria can thereby be prevented, alleviated and/or cured and a promotion in growth and an improvement in feed utilization can thereby be achieved.

The following examples illustrate the invention:
Preparation of the starting compounds:

EXAMPLE A

Ethyl 2-(2,4-dichloro-5-fluoro-3-nitro-benzoyl)-3-ethoxyacrylate (a) 2,4-Dichloro-5-fluoro-3-nitro-benzoic acid

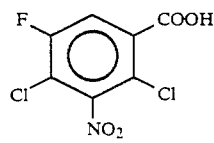

40 ml of concentrated nitric acid are added dropwise to 34 ml of concentrated sulphuric acid, while cooling with ice and stirring. 20.9 g of 2,4-dichloro-5-fluorobenzoic acid are introduced in portions into this nitration mixture, whereupon the temperature rises to 45°-50° C. The mixture is then heated at 90°-100° C. for a further 3 hours, the mixture is cooled to room temperature and poured onto 350 ml of ice-water and the precipitate is filtered off with suction and washed with water. The moist crude product is dissolved hot in 30 ml of methanol, and 150 ml of H₂O were added to the solution. The precipitate is filtered off cold with suction, washed with CH₃OH/H₂O and dried in vacuo at 80° C. 21.2 g of crude 2,4-dichloro-5-fluoro-3-nitro-benzoic acid are obtained. The compound is sufficiently pure for the subsequent reactions. A sample recrystallized from toluene/petroleum ether gives crystals of melting point 192° C.

(b) 2,4-Dichloro-5-fluoro-3-nitro-benzoyl chloride

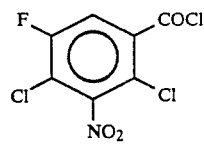

106.6 g of 2,4-dichloro-5-fluoro-3-nitro-benzoic acid are heated at the boiling point under reflux with 250 ml of thionyl chloride for 2 hours. The excess thionyl chloride is then distilled off under normal pressure and the residue is fractionated under a fine vacuum. 104.7 g of 2,4-dichloro-5-fluoro-3-nitro-benzoyl chloride pass over at 110°-115° C./0.08-0.09 mbar. When left to stand, crystals of melting point 35°-37° C. form.

(c) Ethyl (2,4-dichloro-5-fluoro-3-nitro-benzoyl)-acetate

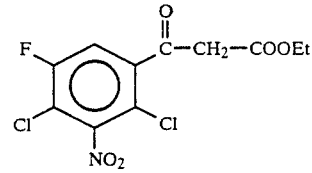

2.1 g of carbon tetrachloride are added to 10.1 g of magnesium filings in 21 ml of etharol and, when the evolution of hydrogen has started, a mixture of 66.6 g of diethyl malonate, 40 ml of ethanol and 150 ml of toluene is added dropwise at 50°-60° C. The mixture is subsequently stirred at this temperature for 1 hour and is cooled to −5° to −10° C. and a solution of 109.2 g of 2,4-dichloro-5-fluoro-3-nitro-benzoyl chluride in 50 ml of toluene is slowly added dropwise. Thereafter, the mixture is stirred at 0° C. for 1 hour, brought tu room temperature overnight and warmed at 40°-50° C. for a "further 2 hours. A mixture of 160 ml of water and 10.4 ml of concentrated sulphuric acid is added to the reaction mixture, while cooling with ice, and the organic phase is separated off. The aqueous phase is extracted with toluene, the combined organic extract is washed with saturated sodium chloride solution and dried with sodium sulphate and the solvent is stripped off. 144.5 g of diethyl (2,4-dichloro-5-fluoro-3-nitro-benzoyl)-malonate are ohtained as a crude product. This is heated under reflux for 3 hours, after addition of 200 ml of water and 0.6 g of 4-toluenesulphonic acid, and the mixture is extracted with methylene chloride and dried with sodium sulphate and the solvent distilled off in vacuo. 118 g of substituted benzoylacetic acid ester are obtained as a crude product. The product is of sufficient purity for the subsequent reactions.

(d) Ethyl 2-(2,4-dichloro-5-fluoro-3-nitro-benzoyl)-3-ethoxyacrylate

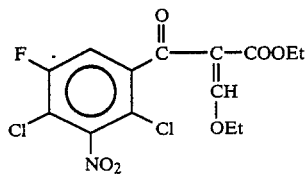

244.8 g of ethyl (2,4-dichloro-5-fluoro-3-nitro-benzoyl)-acetate are heated at 150°-160° C. with 166 g of triethyl orthoformate and 185 g of acetic anhydride for 3 hours. The mixture is then concentrated in vacuo and 270 g of ethyl benzoyl-ethoxy-acrylate are obtained as an oily residue.

EXAMPLE B 2-(2,3,4,5-Tetrafluoro-benzoyl)-3-methoxy-acrylonitrile (a) 2,3,4,5-Tetrafluorophenyl 2-chlorovinyl ketone

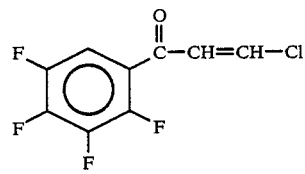

53.2 g of 2,3,4,5-tetrafluorobenzoyl chlorde are added dropwise to a suspension of 36.5 g of anhydrous aluminum chloride in 100 ml of 1,2-dichloroethane at 0°14 10° C., while cooling with ice and stirring. Acetylene is then passed in at 40°-50° C. for 7 hours and the mixture is poured onto ice. The phases are separated, subsequent extraction with methylene chloride is carried out and the extract is washed with water and dried with sodium sulphate. The solvent is distilled off in vacuo and the residue is distilled under a high vacuum. 49.2 g of 2,3,4,5-tetrafluorophenyl 2-chlorovinyl ketone pass over at 92°-105° C./1.5 mbar.

(b) 5-(2,3,4,5-Tetrafluoro)-isoxazole

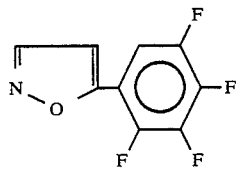

49.2 g of 2,3,4,5-tetrafluorophenyl 2-chlorovinyl ketone and 14.9 g of hydroxylamine hydrochloride are refluxed in 100 ml of methanol for 6 hours. The solvent is distilled off in vacuo, the residue is taken up in methylene chloride/water, the mixture is washed with water and dried with sodium sulphate and lhe solvenl is stripped off in vacuo. 42 g of 5-(2,3,4,5-tetrafluoro)-isoxazole are obtained as a crude product.

(c) 2,3,4,5-Tetrafluorobenzoylacetonitrile

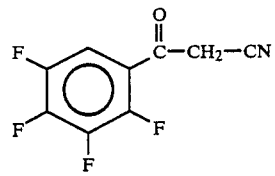

41.8 of crude 5-(2,3,4,5-tetrafluoro)-isoxazole in 60 ml of methanol are added dropwise to a solution of 4.5 g of sodium in 150 ml of methanol, while cooling with ice and stirring. The mixture is stirred at room temperature for 30 minutes and then heated at the boiling point under reflux for 1 hour. The solvent is distilled off in vacuo, the residue is dissolved in water/methylene chloride, the aqueous solution is extracted again wth methylene chloride and the aqueous phase is then acidified to pH 3-4 with 10% strength hydrochloric acid. The mixture is extracted with methylene chloride, the extract is dried with sodium sulphate and the solvent is stripped off in vacuo. The residue is recrystallized from a little methanol. 16.5 g of 2,3,4,5-tetrafluorobenzoyl-acetonitrile of melting point 55°-57° C. are obtained.

d) 2-(2,3,4,5-Tetrafluorobenzoyl)-3-methoxy-acrylonitrile

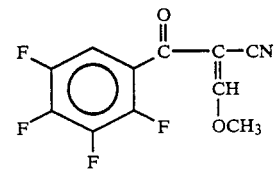

A mixture of 16 g of 2,3,4,5-tetrafluorobenzoylacetonitrile, 15.6 g of trimethyl o-iformate and 18.8 g of acetic anhydride is heated at 150° C. (bath temperature) for 3 hours. The solvent mixture is distilled off completely under a waterpump vacuum and finally under a high vacuum, at a bath temperature of 120° C. 18.2 g of 2-(2,3,4,5-tetrafluorobenzoyl)-3-methoxy-acrylonitrile are obtained as a dark brown oil.

EXAMPLE 1

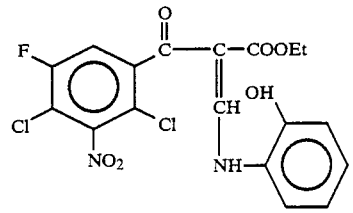

19.0 g of ethyl 2-(2,4-dichloro-5-fluoro-3-nitro-benzoyl)-3-ethoxyacrylate are taken in 20 ml of ethanol. A suspension of 6 g of 2-aminophenol in 40 ml of EtOH is added. The mixture is stirred at room temperature for one hour and the solid which has precipitated is isolated. Yield: 17.8 g of ethyl 2-(2,4-dichloro-5-fluoro-3-nitro benzoyl)-3-(2-hydroxyphenyl-amino)-acrylate.

Melting point: 250°-2° C.(decomposition)

The following aminoacrylic acid esters are obtained analogously to Example 1 (Table 1):

TABLE 1

Aminoacrylic acid esters of the formula II
$R^1, R^2, R^3, R^4 = H$

| Example | $X^1$ | $X^2$ | $X^3$ | $X^4$ | $X^5$ | Z | A | B | D | E | n | m | Y | Melting point |
|---|---|---|---|---|---|---|---|---|---|---|---|---|---|---|
| 2 | F | F | F | F | H | O | CH | CH | CH | CH | 0 | 0 | COOEt | 198–200° |
| 3 | F | Cl | NO$_2$ | Cl | H | O | CH | CH | CF | CH | 0 | 0 | COOEt | 230–2° (D) |
| 4 | F | F | F | F | H | O | CH | CH | CF | CH | 0 | 0 | COOEt | 206–8° |
| 5 | F | F | F | F | H | O | N | CH | CH | CH | 0 | 0 | COOEt | 200–1° |
| 6 | F | Cl | NO$_2$ | Cl | H | O | CH | C—CF$_3$ | CH | CH | 0 | 0 | COOEt | 200–2° |
| 7 | F | F | F | F | H | O | CH | C—NO$_2$ | CH | CH | 0 | 0 | COOEt | 226–8° (D) |
| 8 | F | Cl | NO$_2$ | Cl | H | O | CH | C-Cl | CH | CH | 0 | 0 | COOEt | 170–2° |
| 9 | F | Me | NO$_2$ | Cl | H | O | CH | CH | CH | CH | 0 | 0 | COOEt | 216–18° |
| 10 | F | Cl | NO$_2$ | Cl | H | NAc | CH | CH | CH | CH | 0 | 0 | COOEt | 190–2° |
| 11 | F | Cl | NO$_2$ | Cl | H | O | CH | CH | CH | CH | 1 | 0 | COOEt | 98–100° |
| 12 | F | F | F | F | H | O | CH | CH | CH | CH | 1 | 0 | COOEt | 127–29° |
| 13 | F | F | F | F | H | O | CH | CH | CH | CH | 0 | 1 | COOEt | 128–30° |
| 14 | F | F | F | F | H | O | C—OH | CH | CH | CH | 0 | 0 | COOEt | 264–6° (D) |

D = decomposition

EXAMPLE 15

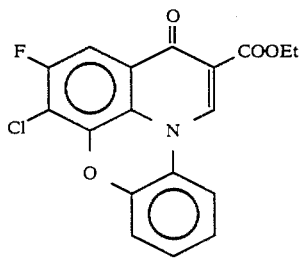

EXAMPLE 28

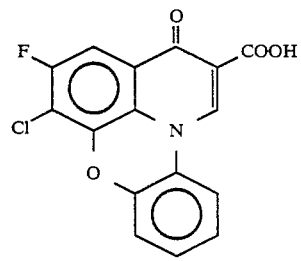

17.8 g of the product from Example 1 and 8.2 g of K$_2$CO$_3$ are heated at 140°–45° C. in 75 ml of dimethylformamide for 3 hours. After cooling to room temperature, the mixture is poured into water. The solid which has precipitated is filtered off with suction and dried at 110° C. Yield: 12.0 g of ethyl 1-chloro-2-fluoro-4-oxo-4H-quino[2,3,4,i,j]-[1,4]-benzoxazine-5-carboxylate Melting point 200°–2° C. (decomposition).

The following quinolonecarboxylic acid esters are obtained analogously to Example 15 (Table 2):

12.0 g of the product from Example 15 are boiled together with 38 ml of acetic acid, 30 ml of water and 3.6 ml of concentrated sulphuric acid for 2 hours. After cooling to room temperature, the mixture is diluted with water. The solid which has precipitated is isolated.

Yield: 10.0 g.

1-Chloro-2-fluoro-4-oxo-4H-quino[2,3,4,i,j][1,4]benzoxazine-5-carboxylic acid

Melting point: >300° C.

TABLE 2

Quinolonecarboxylic acid esters of the formula I
$R^1, R^2, R^3, R^4 = H$

| Example | $X^1$ | $X^2$ | $X^5$ | Z | A | B | D | E | n | m | Y | Melting point |
|---|---|---|---|---|---|---|---|---|---|---|---|---|
| 16 | F | F | H | O | CH | CH | CH | CH | 0 | 0 | COOEt | 214° |
| 17 | F | F | H | O | CH | CH | CF | CH | 0 | 0 | COOEt | 239–40° |
| 18 | F | Cl | H | O | CH | CH | CF | CH | 0 | 0 | COOEt | 208–10° |
| 19 | F | F | H | O | N | CH | CH | CH | 0 | 0 | COOEt | 188–90° (D) |
| 20 | F | Cl | H | O | CH | C—CH$_3$ | CH | CH | 0 | 0 | COOEt | 238–40° (D) |
| 21 | F | F | H | O | CH | C—NO$_2$ | CH | CH | 0 | 0 | COOEt | 286–88° (D) |
| 22 | F | Me | H | O | CH | CH | CH | CH | 0 | 0 | COOEt | 163–66° |
| 23 | F | Cl | H | NH | CH | CH | CH | CH | 0 | 0 | COOEt | 265° (D) |
| 24 | F | F | H | O | CH | CH | CH | CH | 1 | 0 | COOEt | 230–2° |
| 25 | F | Cl | H | O | CH | CH | CH | CH | 1 | 0 | COOEt | 265–67° |
| 26 | F | F | H | O | CH | CH | CH | CH | 0 | 1 | COOEt | 230–2° |
| 27 | F | Cl | H | O | CH | C—Cl | CH | CH | 0 | 0 | COOEt | 190° (D) |

The following quinolonecarboxylic acids were obtained analogously to Example 28 (Table 3):

TABLE 3

Quinolonecarboxylic acids of the formula I
$R^1, R^2, R^3, R^4 = H$

| Example | $X^1$ | $X^2$ | $X^5$ | Z | A | B | D | E | n | m | Y | Melting point |
|---|---|---|---|---|---|---|---|---|---|---|---|---|
| 29 | F | F | H | O | CH | CH | CH | CH | 0 | 0 | COOH | >300° C. |
| 30 | F | F | H | O | CH | CH | CF | CH | 0 | 0 | COOH | 284–88° |
| 31 | F | F | H | O | N | CH | CH | CH | 0 | 0 | COOH | >300° |
| 32 | F | Cl | H | O | CH | C—CF$_3$ | CH | CH | 0 | 0 | COOH | >300° |
| 33 | F | F | H | O | CH | C—NO$_2$ | CH | CH | 0 | 0 | COOH | >300° |

TABLE 3-continued

Quinolonecarboxylic acids of the formula I
$R^1, R^2, R^3, R^4 = H$

| Example | $X^1$ | $X^2$ | $X^5$ | Z | A | B | D | E | n | m | Y | Melting point |
|---|---|---|---|---|---|---|---|---|---|---|---|---|
| 34 | F | Me | H | O | CH | CH | CH | CH | 0 | 0 | COOH | >300° |
| 35 | F | Cl | H | NH | CH | CH | CH | CH | 0 | 0 | COOH | >300° |
| 36 | F | F | H | O | CH | CH | CH | CH | 1 | 0 | COOH | >300° |
| 37 | F | F | H | O | CH | CH | CH | CH | 0 | 1 | COOH | >300° |

It is understood that the specification and examples are illustrative but not limitative of the present invention and that other embodiments within the spirit and scope of the invention will suggest themselves to those skilled in the art.

We claim:

1. A process for the preparation of an enamine of the formula

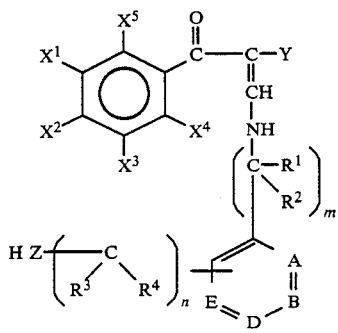

in which
X[1] represents hydrogen, nitro, alkyl with 1-3 carbon atoms or halogen,
X[2] denotes halogen, alkyl with 1-3 carbon atoms, an alkyklsulphonyl group with up to 3 C atoms in the alkyl radical or a phenylsulphonyl group,
R[5] can be hydrogen, halogen or methyl,
R[1], R[2,] R[3] and R[4] each independently represents hydrogen, an alkyl group with 1-3 carbon atoms, phenyl, or a phenyl radical which is substituted by halogen, nitro, or alkyl with up to 3 carbon atoms,
at least two of A, B, D and E representing nitrogen and the balance representing C—H,
Y represents a carboxyl group, a nitrile group an ester group —COOR[5] or an acid amide group —CONR[6]R[7,]
Z represents oxygen or an amine radical NR[8],
m and n each denote 0 or 1,
X[3] represents halogen or the nitro group and
X[4] denotes halogen, a nitro group, an alkoxy, alkylmercapto or alkylsulphonyl group with in each case 1-3 carbon atoms or an arylsulphonyl group,
which comprises reacting an enol ether of the formula

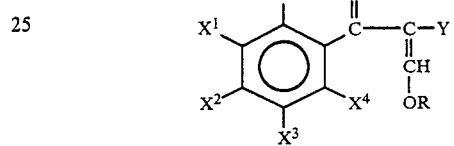

in which
R represents CH$_3$, C$_2$H$_5$ or n-C$_3$H$_7$,
with a primary amine of tho formula

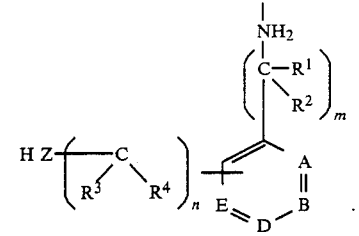

* * * * *

UNITED STATES PATENT AND TRADEMARK OFFICE
CERTIFICATE OF CORRECTION

PATENT NO. : 4,977,263

DATED : December 11, 1990

INVENTOR(S) : Schriewer et al.

It is certified that error appears in the above-identified patent and that said Letters Patent is hereby corrected as shown below:

Title Page  [75] Inventors: After " Klaus " delete " Croche, Glanthal " and substitute -- Grohe, Odenthal -- ; after " Hans " delete " Jonchim Zeiler, Valbert " and substitute -- Joachim Zeiler, Velbert -- ; after " Karl G. " delete " Hetzner " and substitute -- Metzger --

Signed and Sealed this

Sixth Day of October, 1992

Attest:

DOUGLAS B. COMER

*Attesting Officer*          *Acting Commissioner of Patents and Trademarks*